(12) United States Patent
Van den Heuvel (10) Patent No.: US 9,533,143 B2
(45) Date of Patent: Jan. 3, 2017

(54) IMPLANTABLE SOUND SENSOR FOR HEARING PROSTHESES

(75) Inventor: Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 334 days.

(21) Appl. No.: 12/997,788

(22) PCT Filed: Jun. 15, 2009

(86) PCT No.: PCT/US2009/047422
§ 371 (c)(1),
(2), (4) Date: Dec. 13, 2010

(87) PCT Pub. No.: WO2009/152528
PCT Pub. Date: Dec. 17, 2009

(65) Prior Publication Data
US 2011/0112355 A1    May 12, 2011

Related U.S. Application Data

(60) Provisional application No. 61/061,250, filed on Jun. 13, 2008.

(51) Int. Cl.
*A61N 1/36* (2006.01)
(52) U.S. Cl.
CPC .................................. *A61N 1/36032* (2013.01)
(58) Field of Classification Search
CPC . A61N 1/36032; A61F 11/045; H04R 25/606; H04R 2460/13; H04R 2225/67; H04R 1/00
(Continued)

(56) References Cited

U.S. PATENT DOCUMENTS

| 4,729,366 A | 3/1988 | Schaefer |
| 5,814,095 A * | 9/1998 | Muller et al. .................. 607/57 |

(Continued)

FOREIGN PATENT DOCUMENTS

| DE | 10030372 A1 * | 1/2002 | .......... H04R 25/606 |
| WO | WO 2006/058368 | 6/2006 | |
| WO | 2007/023164 | 3/2007 | |

OTHER PUBLICATIONS

Zou et al. ("Single- and Triaxis Piezoelectric-Bimorph Accelerometers", Journal of Microelectromechanical Systems, vol. 17, No. 1 (2009).*

(Continued)

*Primary Examiner* — Jacqueline Cheng
*Assistant Examiner* — Kaylee Wilson
(74) *Attorney, Agent, or Firm* — Hauptman Ham, LLP (57) ABSTRACT

A sound sensor implantable in a recipient of a hearing device. The sound sensor comprises a biocompatible housing comprising a cavity having an opening at a first end of the housing, and a membrane attached to the housing so as to hermetically seal the opening. The membrane vibrates in response to vibration of at least on a structure of the recipient's ear and fluid within one of the recipient's body cavities. The sound sensor also comprises a vibrational sensor disposed in the housing configured to detect vibrations of the membrane, and configured to generate signals representative of the detected vibrations; and a transmitter configured to provide the generated signals to one or more other components implanted in the recipient.

30 Claims, 6 Drawing Sheets

(58) Field of Classification Search
 USPC .......................................................... 600/25
 See application file for complete search history.

(56) References Cited

U.S. PATENT DOCUMENTS

| | | | |
|---|---|---|---|
| 6,005,955 A * | 12/1999 | Kroll .................... | H04R 25/606 |
| | | | 381/312 |
| 6,193,645 B1 | 2/2001 | Kennedy | |
| 6,516,228 B1 * | 2/2003 | Berrang et al. ................. | 607/57 |
| 6,626,822 B1 | 9/2003 | Jaeger et al. | |
| 2001/0003788 A1 * | 6/2001 | Ball et al. ........................ | 600/25 |
| 2001/0007050 A1 * | 7/2001 | Adelman ...................... | 600/150 |
| 2001/0016678 A1 | 8/2001 | Kennedy | |
| 2002/0026091 A1 * | 2/2002 | Leysieffer ...................... | 600/25 |
| 2002/0071585 A1 | 6/2002 | Miller | |
| 2003/0125602 A1 | 7/2003 | Sokolich et al. | |
| 2004/0039245 A1 * | 2/2004 | Jaeger ................. | H04R 25/606 |
| | | | 600/25 |
| 2004/0243212 A1 | 12/2004 | Dadd et al. | |
| 2005/0049641 A1 * | 3/2005 | Shah et al. ........................ | 607/2 |
| 2005/0101831 A1 * | 5/2005 | Miller et al. ..................... | 600/25 |
| 2006/0058573 A1 * | 3/2006 | Neisz et al. ..................... | 600/25 |
| 2006/0178553 A1 * | 8/2006 | Neisz et al. ..................... | 600/25 |
| 2006/0183965 A1 * | 8/2006 | Kasic et al. ..................... | 600/25 |
| 2007/0274558 A1 * | 11/2007 | Lyon .................... | H04R 19/013 |
| | | | 381/424 |

OTHER PUBLICATIONS

International Search Report, for PCT/US2009/047422, mailed Jul. 29, 2009, 2 pages.
Written Opinion, for PCT/US2009/047422, mailed Jul. 29, 2009, 5 pages.
International Preliminary Report on Patentability, for PCT/US2009/047422, mailed Jun. 11, 2010, 10 pages.
Chinese Office Action for Chinese Application No. 200980129299.8 mailed Apr. 1, 2013 along with an English translation (7 pages).
European Search Report and Search Opinion, Application No. 09763815.9 mailed Dec. 9, 2011 (7 pages).

\* cited by examiner

IMPLANTABLE SOUND SENSOR FOR HEARING PROSTHESES

CROSS-REFERENCE TO RELATED APPLICATIONS

This application is a National Stage Application of International Application No. PCT/US2009/047422 filed Jun. 15, 2009, and claims priority to U.S. Provisional Application No. 61/061,250, filed Jun. 13, 2008.

BACKGROUND

Field of the Invention

The present invention relates generally to implantable sound sensors, and more particularly, to an implantable sound sensor for hearing prostheses.

Related Art

Implantable hearing prostheses primarily comprise an implantable stimulator that provides electrical, mechanical, optical or other stimulation to a recipient's inner and/or middle ear. Such prostheses also include a microphone, that is configured to receive and transform an acoustic sound into an electrical signal that is supplied to a sound processor. The sound processor utilizes the signal to drive the implantable stimulator.

One type of implantable hearing prosthesis, referred to as a cochlear implant, delivers electrical signals to a recipient's auditory nerves via electrodes implanted in the recipient's cochlea. The delivered electrical signals cause the recipient's brain to perceive a hearing sensation resembling the natural hearing sensation normally delivered by the auditory nerve. Another type of implantable hearing prosthesis is the auditory brainstem implant that delivers electrical stimulation signals directly to a recipient's brain, thereby bypassing the auditory nerve. A still other type of implantable hearing prosthesis is the middle ear implant that uses an actuator to provide mechanical stimulation signals (vibration) to a recipient's middle or inner ear.

In some implantable hearing prostheses, the microphone is also implanted in the recipient. Implantable microphones are conventionally implanted subcutaneously in proximity of the ear. A drawback of subcutaneous microphones is that they are sensitive to body noise which may originate from the circulatory, respiratory, skeletal, digestive or other systems.

SUMMARY

In accordance with one embodiment of the present invention, a sound sensor implantable in a recipient of a hearing device is disclosed. The sound sensor comprises a biocompatible housing comprising a cavity having an opening at a first end of the housing; a membrane attached to the housing so as to hermetically seal the opening, wherein the membrane vibrates in response to vibration of at least one of a structure of the recipient's ear and fluid within one of the recipient's body cavities; a vibrational sensor disposed in the housing configured to detect vibrations of the membrane, and configured to generate signals representative of the detected vibrations; and a transmitter configured to provide the generated signals to one or more other components implanted in the recipient.

In accordance with another embodiment of the present invention, an implantable hearing prosthesis is disclosed. The hearing prosthesis comprises: an implantable unit comprising a sound processor and a stimulator unit configured to generate stimulation signals for delivery to a recipient's ear; and an implantable sound sensor, comprising: a biocompatible housing comprising a cavity having an opening at a first end of the housing; a membrane attached to the housing so as to hermetically seal the opening, wherein the membrane vibrates in response to vibration of at least one of a structure of the recipient's ear and fluid within one of the recipient's body cavities; a vibrational sensor disposed in the housing configured to detect vibrations of the membrane, and to generate signals representative of the detected vibrations; and a transmitter configured to provide the generated signals to the stimulator unit.

BRIEF DESCRIPTION OF THE DRAWINGS

Embodiments of the present invention are described below with reference to the attached drawings, in which.

DETAILED DESCRIPTION

Aspects of the present invention are generally directed to sound sensor implantable in a recipient of a hearing device. The sound sensor is configured to detect sound through the use of vibrations of structures of the recipient's ear, or through pressure variations that occur in the recipient's body cavities.

In embodiments of the present invention, the sensor comprises a hermetically sealed biocompatible housing having a membrane attached thereto. The membrane is configured to vibrate in response to vibration of at least on a structure of the recipient's ear and fluid within one of the recipient's body cavities. A vibrational sensor, disposed in the housing, and detects vibrations of the membrane and generates signals representative of the detected vibrations.

Embodiments of the present invention are described herein primarily in connection with one type of implantable hearing prosthesis, namely a totally or fully implantable cochlear prosthesis (commonly referred to as a cochlear prosthetic device, cochlear implant, cochlear device, and the like; simply "cochlear implants" herein). As used herein, a totally implantable cochlear implant refers to an implant that is capable of operating, at least for a period of time, without the need for any external device. It would be appreciated that embodiments of the present invention may also be implemented in a cochlear implant that includes one or more external components. It would be further appreciated that embodiments of the present invention may be implemented in any partially or fully implantable hearing prosthesis now known or later developed, including, but not limited to, acoustic hearing aids, auditory brain stimulators, middle ear mechanical stimulators, hybrid electro-acoustic prosthesis or other prosthesis that electrically, acoustically and/or mechanically stimulate components of the recipient's outer, middle or inner ear.

Figure 1:
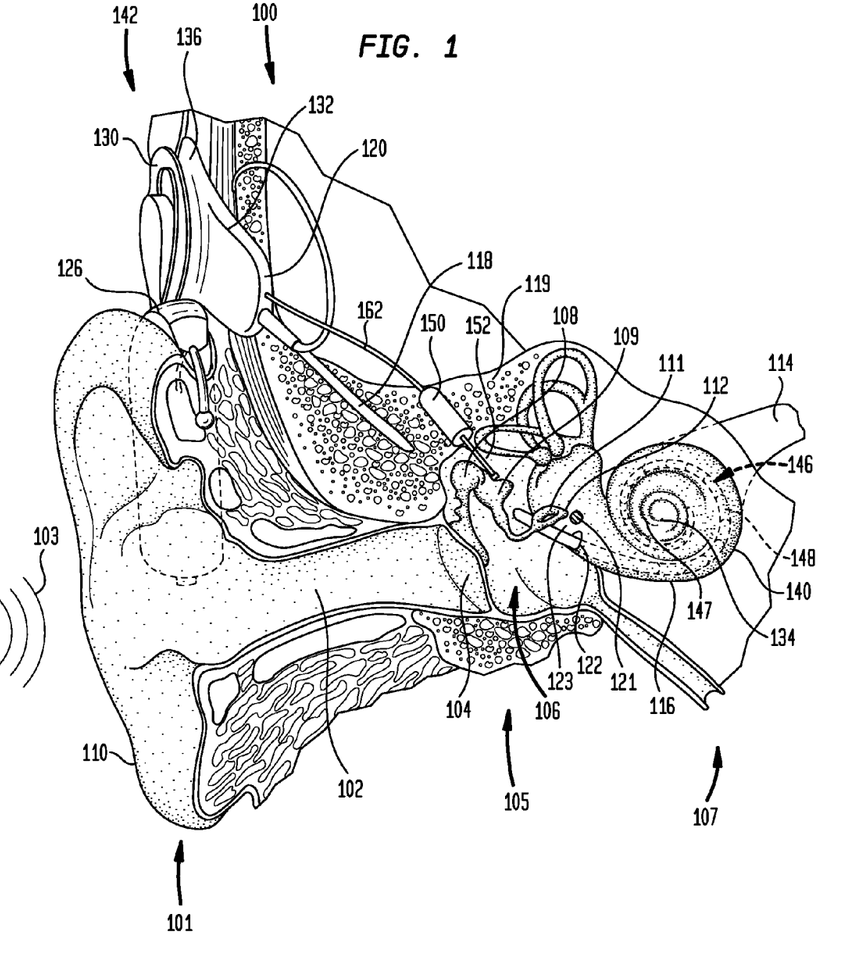
FIG. 1 is a perspective view of an exemplary totally implantable cochlear implant, in which embodiments of the present invention may be implemented.

FIG. 1 is perspective view of a totally implantable cochlear implant, referred to as cochlear implant 100, implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142 which, as described below, is configured to provide power to the cochlear implant.

In the illustrative arrangement of FIG. 1, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. As would be appreciated, various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire. Positioned substantially within the wire coils is an implantable microphone system (not shown). As described in detail below, the implantable microphone assembly includes a microphone (not shown), and a magnet (also not shown) fixed relative to the internal coil.

Cochlear implant 100 further comprises a main implantable component 120 and an elongate electrode assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. As noted, a stimulator unit generates stimulation signals which are applied by electrodes 148 to cochlea 140, thereby stimulating auditory nerve 114.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

Stimulator 132 receives a signal generated by an implanted sound sensor 150, in this embodiment, via a cable 162. Sound sensor 150 is implanted in a cavity formed in mastoid bone 119 so as to extend, in this embodiment, into the middle ear cavity. Sound sensor 150 is configured to detect sound received in a recipient's ear through the use of vibrations or pressure variations that occur in or along the natural path that is followed by acoustic waves in the ear. More specifically, sound sensor 150 senses vibration of a structure of the recipient's ear or vibration of fluid within one of the recipient's body cavities, such as recipient's middle ear cavity, inner ear canals, cochlear ducts, etc. The vibration of the recipient's ear structure, or the vibration of the fluid within a body cavity is a result of the receipt of acoustic waves that travel from the recipient's outer ear to the middle and inner ear. That is, the received acoustic waves result in the vibration of the middle or inner ear structures, or travel through the middle ear cavity, creating vibration of the fluid within the cavities. In the embodiment illustrated in FIG. 1, the sound sensor detects sound based on vibration of the recipient's middle ear bones, and more specifically, based on vibration of incus 109.

An embodiment of implantable sound sensor 150 is described next below with reference to FIGS. 2A and 2B, referred to herein as implantable sound sensor 250. Implantable sound sensor 250 comprises a housing 258 having, in this embodiment, a substantially tubular shape. The tubular shape may have a cylindrical or elliptical cross-sectional shape. Other shapes, such as prismatic with square, rectangular, or other polygonal cross-sectional shapes may also be used in alternative embodiments. However, a cylindrical shape may be advantageous for purposes of implantation and manufacture.

Figure 2A:
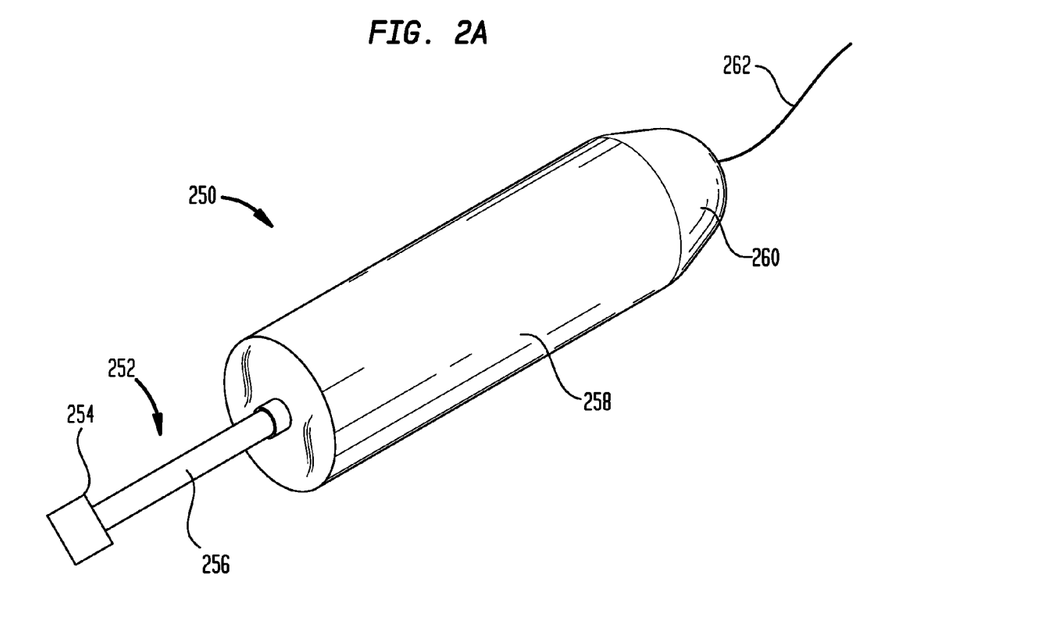
FIG. 2A is a perspective view of an implantable sound sensor in accordance with embodiments of the present invention.
Figure 2B:
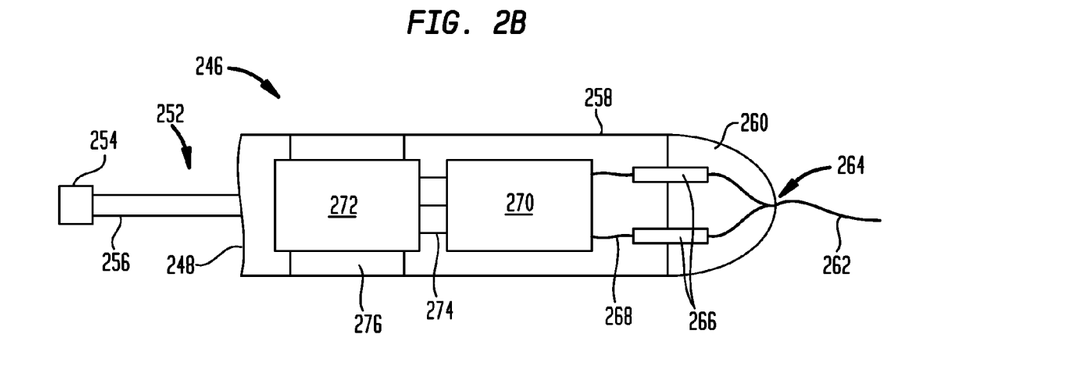
FIG. 2B is a longitudinal cross-sectional view of the sound sensor of FIG. 2A, illustrating the primary components in a functional block diagram, in accordance with embodiments of the present invention.

In the embodiments of FIGS. 2A and 2B, housing 258 is closed at one end 246 by a membrane 248. Membrane 248 is connected to housing 258 as to hermetically seal the one end 246. Membrane 248 may be connected to housing 258 through one of many known techniques, such as laser welding, or manufacturing (milling, turning) housing 258 and membrane 248 out of one piece.

Housing 258 is closed at the opposing end 264, that is, the end remote from membrane 248, by a closure 260. Closure 260 also provides a hermetical seal. Hence, housing 258, membrane 248 and closure 260 form a biocompatible hermetically sealed enclosure that is substantially impenetrable to air and body fluids.

In embodiments of the present invention, membrane 248 is substantially flexible and is configured to vibrate. The thickness of membrane 248 is selected depending on, for example, the material of which it is made and the body location in which sound sensor 250 will be implanted. Additionally, membrane 248 and housing 258 may be each made from the same or different titanium or a titanium alloy. However, it would be appreciated that other biocompatible materials may also be used. For example, in one alternative embodiment, closure 260 may be manufactured of a biocompatible ceramic material.

A coupling mechanism 252 is secured to the exterior surface of membrane 248. In the embodiment illustrated in FIGS. 2A and 2B, coupling mechanism 252 comprises an elongate rod 256 and a bracket 254 disposed on the distal end of the rod. Bracket 254 may have a variety of configurations depending on which structure of the natural ear the device is to be secured. This is described in further detail below.

A vibrational sensor 272, such as a microphone, is disposed inside housing 258. In certain such embodiments, vibrational sensor is a pressure sensitive transducer configured to generate an electrical signal in response to detected pressure waves. Microphone 272 may be arranged such that the microphone's sensing element is located proximal to membrane 248 with a defined gas layer 275 positioned between the microphone's sensing element and the membrane. The microphone's sensing element is typically a diaphragm.

In the above embodiments, as coupling mechanism 252 vibrates membrane 248, the excitation of the membrane is transmitted to the inside of housing 258, where it is sensed by microphone 272. Microphone 272 may be an electret microphone, such as from Sonion (Denmark) or Knowles (USA). Other types of microphones may be used as well, such as: magnetic, dynamic, piezo-electric, optical, or electro-mechanical.

In an alternative embodiment, vibrational sensor 272 is an accelerometer suitable for sensing vibrations of membrane 248. In one particular embodiment, vibrational sensor 272 is a micro-electromechanical system accelerometer.

Vibrational sensor 272 is connected to housing 258 by means of a fluid suspension 276, which is preferably made of, or that comprises, silicone. It should be appreciated that in alternative embodiments other mechanisms may be implemented to isolate vibrational sensor 272 from the motion of sound sensor 250.

Implantable sound sensor 250 further comprises a transmitter for transmitting the signal generated by vibrational sensor 272, either raw or processed, to an element outside of sound sensor 250, such as to an implantable stimulation device or other component of an implantable hearing prosthesis.

The transmitter may comprise an electronic circuit 270 mounted inside housing 258 that is coupled to microphone 272 by wires 262. Electronic circuit 270 may be configured to process the signal generated by the microphone 272 for transmission to an implantable stimulation device.

Electronic circuit 270 may be configured to convert alternating electrical current (AC) to direct electrical current (DC) and to deliver electrical power to the microphone 272. In the embodiment of FIGS. 2A and 2B, electrical power is provided from a source outside of sensor 250 through wires 262 (through AC current). In alternative embodiments, a battery can be provided inside housing 258.

At least one feed through 266 is preferably provided for passing electrical wires 262 to through housing 258. Feed through 266 is preferably provided through closure 260. In certain embodiments, feed through 266 is formed in closure 260; in other words, they are unitary.

Electrical wires 262 may be configured to pass electrical power to implantable device 250. Wires 262 may be configured to transmit the processed microphone signal to the exterior of sound sensor 250. In the latter case, electronic circuit 270 may be configured to modulate the signal on the power wires.

In an alternative embodiment, the transmission is wireless. In such embodiments the implantable device 250 may be provided with an electromagnetic antenna (not shown).

The enclosure, formed by housing 258, membrane 248 and closure 260, is, in certain embodiments, filled with an inert gas, such as nitrogen or argon.

In the embodiment illustrated in FIGS. 1, 2A and 2B, rod 256 is an elongate member suitable for coupling membrane 248 to a vibrating structure of the ear. Alternatively, the sound sensor 250 may comprise one or more brackets 254 for additionally connecting membrane 248 to a structure of the middle or inner ear. In certain embodiments, rod 256 or bracket 254 may be coupled to the tympanic membrane, and bracket 254 may be a bracket similar to those used for tympanoplasty. That is, bracket 254 may comprise a disc for coupling to the tympanic membrane. Additionally, in other embodiments rod 256 or bracket 254 may be coupled to the malleus, the incus, or the stapes, and bracket 254 may comprise, for example, a bracket such as those used for stapedioplasty. In such embodiments, bracket 254 comprises a clip for coupling to one of those structures. In still other embodiments, rod 256 or bracket 254 may be coupled to the elliptical window, round window, the horizontal canal, the posterior canal or the superior canal. In embodiments of the present invention, bracket 254 is coupled to the membrane 248 in the middle thereof, may be positioned to influence the dynamics of the membrane, or may be positioned to increase membrane sensitivity.

Figure 3A:
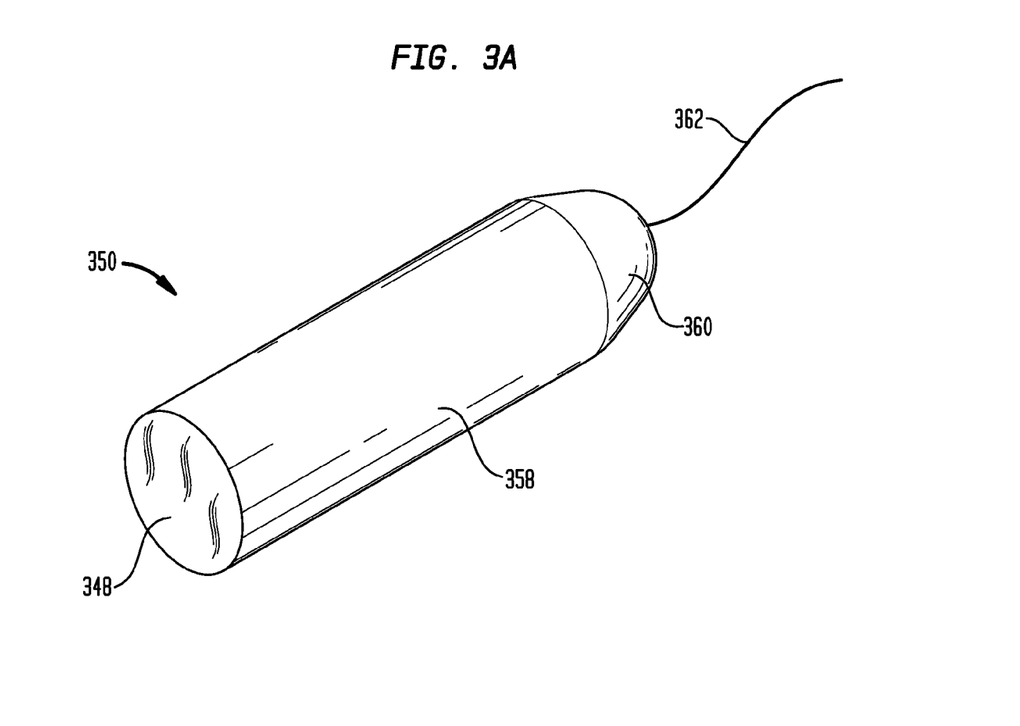
FIG. 3A is a perspective view of an implantable sound sensor in accordance with embodiments of the present invention.
Figure 3B:
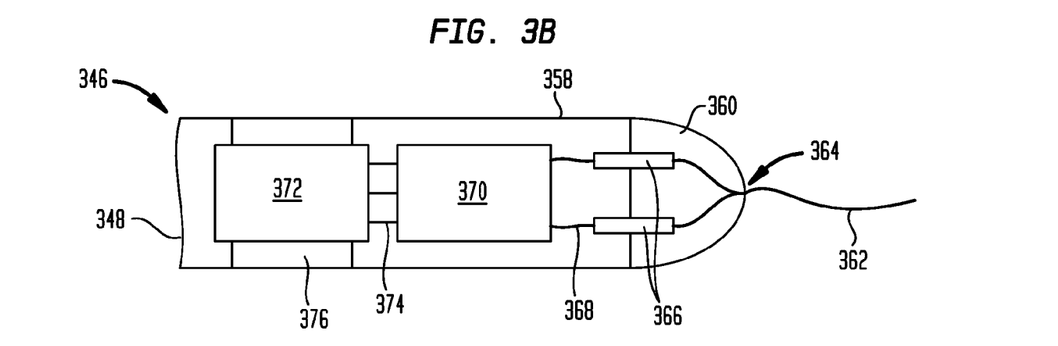
FIG. 3B is a longitudinal cross-sectional view of the sound sensor of FIG. 3A, illustrating the primary components in a functional block diagram, in accordance with embodiments of the present invention.

FIGS. 3A and 3B are perspective and functional block diagrams, respectively, of an alternative embodiment of sound processor 150, referred to herein as sound processor 350. Sound sensor 350 has a membrane 348 with no coupling mechanism to physically couple the membrane to a vibrating structure of the recipient's ear. Rather, sound sensor 350 is configured to be implanted so as to be exposed to a natural cavity (or "hollow" organ) of the ear. Such a cavity may be the middle ear cavity, the cochlea or external ear canal. Such cavity is preferably a cavity of the middle ear. The cavity refers to an organ, or part of an organ of the ear, that is filled with a fluid. In particular, the fluid is a gas as in the middle ear cavity, or a liquid, as in the cochlea.

In the illustrative embodiments of FIGS. 3A and 3B, membrane 348 is sufficiently flexible and is configured to vibrate in response to pressure variations in the cavity to which the membrane is exposed. The thickness of the membrane is selected depending on, for example the material of which it is made, the likely location of sensor 350 within a recipient, the likely cavity to which membrane 348 may be exposed, etc. Membrane may be made from titanium or a titanium alloy.

As used herein, the terms "sound" and "acoustic waves" refer to pressure waves, which can be perceived by the hearing organ of a healthy person or animal (mammal). Sound in the a frequency spectrum between about 20 Hz and 20 kHz is generally perceivable by a human having normal, functional hearing.

Implantable sound sensors according to certain embodiments of the present invention are configured as to enable a surgeon to surgically implant the implantable sound sensors with relative ease when compared to conventional surgical procedures for implantation of devices adjacent a recipient's middle or inner ears. For example, this relatively easy surgical method is generally to drilling a canal from the outside of a patient's head to the location where the distal end of the housing 258, 358 is exposed to the relevant cavity, and/or coupling mechanism 252 is secured to the desired vibrating structure of the ear. Next, implantable sound sensor 250, 350 is secured to the recipient.

It is generally desirable that the size of the drilled canal be kept as small as possible. As such, the implantable sound sensors according to certain embodiments of the invention have a small aspect ratio. As is well know, the aspect ratio of a device refers to ratio of the device's width to the device's height. The length of the implantable sensors refers to the total size, measured along the longitudinal axis of the elongate housing, from membrane 248, 348 to, and including, closure 260,360, respectively. In determining the length of the implantable device, the length of any external wires protruding out of closure 260,360 are not included. The breadth or width of the implantable sound sensor refers to the smallest dimension of the cross-section of the sensor measured perpendicular to the longitudinal axis of the tubular housing. In embodiments of the present invention, the aspect ratio of the breadth (width) to the length of the implantable device 250, 350 is smaller than 1. The housing 258, 358 have thus preferably an elongate shape.

In certain embodiments of the present invention, the aspect ratio of the breadth to the length of the implantable sensor 250, 350 is smaller than or equal to 0.75. In specific such embodiments, the aspect ratio of sensor 250, 350 is smaller than or equal to 0.6, while in still other embodiments the aspect ratio is smaller than or equal to 0.45.

The size of the membrane refers to the smallest dimension (diameter in the case of a membrane having a circular cross-sectional shape) of the membrane measured perpendicular to the longitudinal axis of the tubular housing. In certain embodiments, the size of membrane 248, 348 is smaller than or equal to 9 mm. In certain such embodiments, membrane 248, 348 has a size smaller than or equal to 7 mm, while in still other embodiments the membrane has a size smaller than or equal to 5 mm, or a size smaller than or equal to 3.5 mm.

In embodiments of the present invention, the length of sensor 250, 350 is smaller than or equal to 20 mm. In specific embodiments, sensor 250, 350 has a length smaller than or equal to 15 mm, or a length smaller than or equal to 12.5 mm. Sensors according to embodiments of the present invention that have a small aspect ratio device provide several benefits. One advantage is that surgical implantation is simplified and the extent of intervention is reduced. A second advantage is that the small breadth of the sensor allows full exposure of the membrane in various cavities of the ear, in particular, exposure in the middle ear cavity. Furthermore, in embodiments in which the membrane is not skin loaded, the attenuation of acoustic waves arriving at the membrane 248, 348 is reduced, resulting in a smaller membrane needed for an equal sensitivity. Finally, the directionality of the acoustic waves, induced by the outer ear, can be fully exploited.

As previously noted, sensor 250, 350 is fixed to the recipient. Sensor 250, 350 may, in certain embodiments, be fixed to a bony structure, such as the temporal bone. This fixation may be performed out by conventional brackets known in the art. Such brackets are configured to be attached to housing 248, 348 and hence provide mechanical coupling between the housing and the bony structure.

Figure 4A:
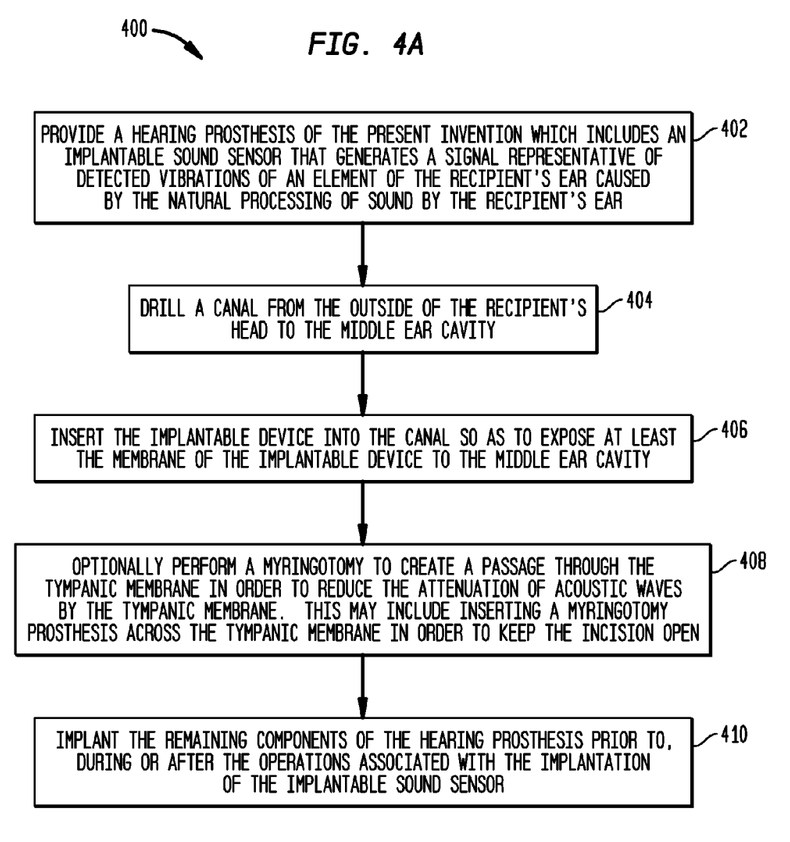
FIG. 4A is a flow chart of the operations performed to implant an embodiment of a hearing prosthesis having an embodiment of a sound sensor, in accordance with embodiments of the present invention.
Figure 4B:
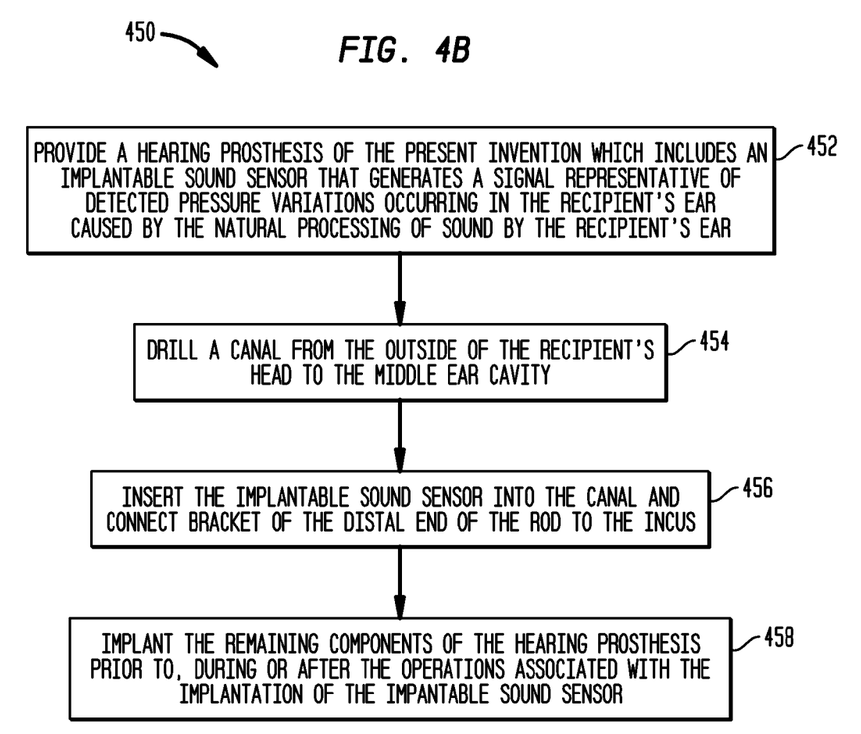
FIG. 4B is a flow chart of the operations performed to implant another embodiment of a hearing prosthesis having an embodiment of a sound sensor, in accordance with embodiments of the present invention.
Figure 5:
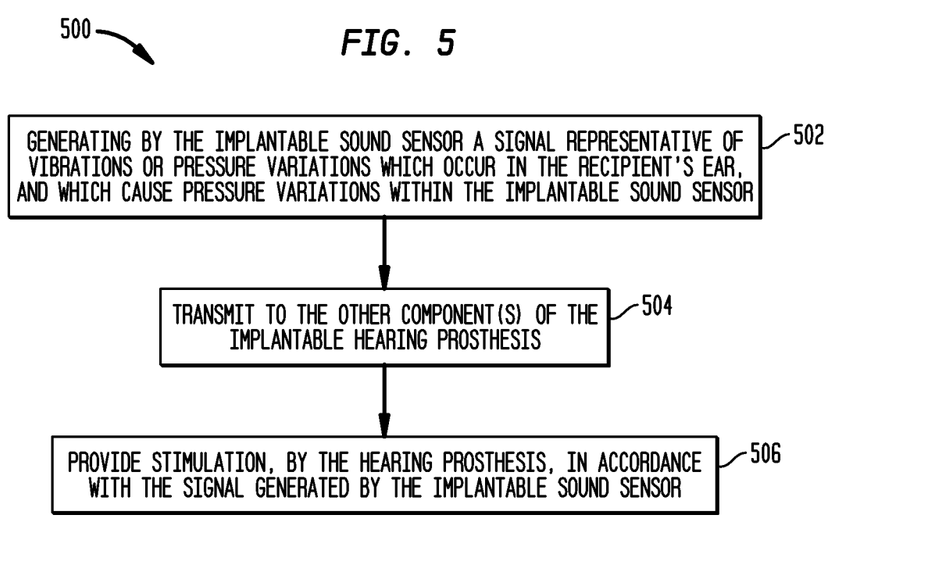
FIG. 5 is a flow chart of the operations performed during operation of an embodiment of a hearing prosthesis having an embodiment of a sound sensor.

FIGS. 4A and 4B are flow charts of the operations performed to implant a hearing prosthesis having an embodiment of a sound sensor, in accordance with embodiments of the present invention. FIG. 5 is a flow chart of the operations performed during operation of a hearing prosthesis having an embodiment of a sound sensor in accordance with aspects of the present invention.

The method begins at step 402 with a hearing prosthesis having an implantable sound sensor in accordance with aspects of the present invention is provided. At step 404, a canal is formed such as by drilling from the outside of the patient's head to the middle ear cavity. At step 406, the implantable device (sensor) is inserted into the canal so as to expose at least the membrane of the implantable device to the middle ear cavity. At step 408 a myringotomy may optionally be performed to create a passage through the tympanic membrane in order to reduce the attenuation of acoustic waves by the tympanic membrane. This may include inserting a myringotomy prosthesis across the tympanic membrane in order to keep the incision open.

Then, at step 410, the other components of the hearing prosthesis are implanted. As would be appreciated, the order of steps in FIG. 4A are merely illustrative and the other components of the hearing prosthesis may be implanted prior to, during or after the operations of steps 404, 406 and optionally 408 associated with the implantation of the implantable sound sensor.

FIG. 4B is a flowchart illustrating an alternative method 450 in accordance with embodiments of the present invention. As shown, method 450 includes steps 402, 404, 406 and 410 of FIG. 4A. However, after insertion of the sound sensor at step 406, in method 450 at step 452 the sound sensor is connected to an element of the recipient's ear.

FIG. 5 is a flowchart showing the operations performed during normal use of a hearing device including a sound sensor in accordance with embodiments of the present invention. First, at step 501, an implantable sound sensor senses vibration of at least one of an element of a recipient's ear and of fluid within one of the recipient's body cavities. At step 502, the implantable sound sensor generates a signal representative of the sensed vibrations or.

At step 504, the signal generated by the sound sensor is transmitted to one or more other components of the hearing prosthesis. At step 506 the hearing prosthesis provides stimulation based on the signal generated by the implantable sound sensor.

In certain embodiments of the present invention, the sound sensor may be fixed, via a bracket, in or adjacent to inner ear cavity. For example, the sound sensor may be positioned adjacent the elliptical window, circular (round) window, the horizontal canal, the posterior canal or the superior canal.

In accordance with embodiments of the present invention, the housing of the sound sensor has a cylindrical cross-sectional shape and has a diameter (breadth/width) of about 3.5-4 mm. The length of such a sensor may be about 10-15 mm. This allows an electret microphone, such as a Sonion 8009, having an outer diameter of 2.56 mm and a length of 3 mm to be positioned within the housing of the sound sensor. The electronic circuitry for AC-DC conversion may be provided on a board or chip that also fits within the housing and may, in certain embodiments, have length that does not exceed 3 mm.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A sound sensor implantable in a recipient of a hearing device, the sound sensor comprising:
 a biocompatible housing comprising a cavity having an opening at a first end of the housing;
 a membrane attached to the housing so as to hermetically seal the opening, the membrane being configured to vibrate in response to vibration of a structure of the recipient's middle or inner ear;
 a first coupling mechanism configured to mechanically couple the housing to a stationary bony structure of the recipient;
 a second coupling mechanism configured to mechanically couple the membrane to the structure of the recipient's middle or inner ear;
 a vibrational sensor, disposed in the housing, the vibrational sensor being configured to:
  detect vibrations of the membrane; and
  generate signals representative of the detected vibrations; and
 a transmitter disposed inside the biocompatible housing and configured to provide the generated signals to one or more other components implanted in the recipient.

2. The sound sensor of claim 1, wherein the vibrational sensor comprises: an accelerometer.

3. The sound sensor of claim 1, wherein the vibrational sensor comprises: a pressure sensor positioned proximate to the membrane, wherein a defined gas layer is disposed between the pressure sensor and the membrane.

4. The sound sensor of claim 1, wherein the second coupling mechanism comprise a bracket configured to connect a rod to the recipient's tympanic membrane.

5. The sound sensor of claim 1, wherein an aspect ratio of the sensor is less than or equal to approximately 0.75.

6. The sound sensor of claim 1, wherein the membrane is circular and has a diameter that is less than or equal to approximately 9 mm.

7. The sound sensor of claim 1, further comprising: a suspension of fluid, wherein the vibrational sensor is coupled to the housing via the fluid suspension.

8. The sound sensor of claim 7, wherein the fluid suspension comprises silicone.

9. The sound sensor of claim 1, wherein an aspect ratio of the sensor is less than or equal to approximately 0.45.

10. The sound sensor of claim 9, wherein an length of the sensor is smaller than or equal to approximately 15 mm.

11. The sound sensor of claim 1, wherein the membrane is circular and has a diameter that is less than or equal to approximately 5 mm.

12. The sound sensor of claim 1, wherein the membrane is circular and has a diameter that is less than or equal to approximately 3.5 mm.

13. The sound sensor of claim 1, wherein an aspect ratio of the sensor is less than or equal to approximately 0.6.

14. The sound sensor of claim 1, wherein the second coupling mechanism comprises: an elongate apparatus having proximal end connected to the membrane and a distal end, wherein the sound sensor is configured such that the elongate apparatus is a free-standing member relative to all other components of the sound sensor other than the membrane.

15. The sound sensor of claim 1, wherein the second coupling mechanism includes a rod that is longer than a diameter of the membrane.

16. The sound sensor of claim 1, wherein the sound sensor is configured such that the vibration sensor is completely free of direct contact with the membrane.

17. The sound sensor of claim 1, wherein the vibration sensor is completely spaced away from the membrane.

18. The sound sensor of claim 1, wherein the vibration sensor is a microphone.

19. The sound sensor of claim 1, wherein the vibration sensor is an electret sensor.

20. The sound sensor of claim 1, wherein the sound sensor is configured such that the membrane is completely free to move in both directions along a longitudinal axis of the sound sensor with resistance corresponding to an amount at least equal to that which results from tension of the membrane and pressure inside the sound sensor.

21. The sound sensor of claim 1, wherein the sound sensor is configured such that during operation of the vibration sensor, the vibration sensor is completely free of direct contact with the membrane.

22. An implantable hearing prosthesis, comprising:
an implantable unit comprising a sound processor and a stimulator unit configured to generate stimulation signals for delivery to a recipient's ear; and
an implantable sound sensor, comprising:
a biocompatible housing comprising a cavity having an opening at a first end of the housing;
a membrane attached to the housing so as to hermetically seal the opening, the membrane being configured to vibrate in response to vibration of a structure of the recipient's middle or inner ear;
a first coupling mechanism configured to mechanically couple the housing to a stationary bony structure of the recipient;
a second coupling mechanism configured to mechanically couple the membrane to the structure of the recipient's middle or inner ear;
a vibrational sensor disposed in the housing, the vibrational sensor being configured to:
detect vibrations of the membrane; and
generate signals representative of the detected vibrations; and
a transmitter disposed inside the biocompatible housing and configured to provide the generated signals to the stimulator unit, wherein
the coupling mechanism includes an elongate member having a proximal end connected to the membrane and a distal end, wherein the elongate member is configured to be securely connected at the distal end to the structure of the recipient's middle or inner ear, thereby conveying vibration of the structure of the recipient's middle or inner ear to the membrane.

23. The hearing prosthesis of claim 22, wherein the structure of the recipient's middle or inner ear comprises a portion of one or more of the recipient's middle ear and the recipient's inner ear that vibrates in response to sound received by the recipient's outer ear.

24. The hearing prosthesis of claim 22, wherein the vibrational sensor comprises: an accelerometer.

25. The hearing prosthesis of claim 22, wherein the vibrational sensor comprises: a pressure sensor positioned proximate to the membrane, wherein a defined gas layer is disposed between the pressure sensor and the membrane.

26. The hearing prosthesis of claim 22, further comprising: a suspension of fluid, wherein the vibrational sensor is coupled to the housing via the fluid suspension.

27. A sound sensor implantable in a recipient of a hearing device, the sound sensor comprising:
a biocompatible housing comprising a cavity having an opening at a first end of the housing;
a membrane attached to the housing so as to hermetically seal the opening, the membrane being configured to vibrate in response to vibration of fluid within one of the recipient's body cavities of the recipient's middle or inner ear;
a coupling mechanism configured to mechanically couple the housing to a stationary bony structure of the recipient;
a vibrational sensor, disposed in the housing, the vibrational sensor being configured to:
detect vibrations of the membrane; and
generate signals representative of the detected vibrations; and
a transmitter disposed inside the biocompatible housing and configured to provide the generated signals to one or more other components implanted in the recipient, wherein an aspect ratio of the sound sensor is less than or equal to approximately 0.75.

28. The sound sensor of claim 27, wherein the aspect ratio of the sensor is less than or equal to approximately 0.45.

29. The sound sensor of claim 27, wherein the membrane is circular and has a diameter that is less than or equal to approximately 5 mm.

30. The sound sensor of claim 27, wherein there is no coupling mechanism present to physically couple the membrane to a vibrating structure of the recipient.

* * * * *